United States Patent [19]

Merchant et al.

[11] Patent Number: 5,791,338
[45] Date of Patent: Aug. 11, 1998

[54] ENDOTRACHEAL INTUBATION APPARATUS

[75] Inventors: William T. Merchant, 925 Hartman La., Lebanon, Pa. 17042; Guy G. Gerberich, Jonestown, Pa.

[73] Assignee: William T. Merchant, Lebanon, Pa.

[21] Appl. No.: 587,752

[22] Filed: Jan. 17, 1996

Related U.S. Application Data

[63] Continuation-in-part of Ser. No. 187,609, Jan. 26, 1994, abandoned.

[51] Int. Cl.⁶ ............................................. A61M 16/00
[52] U.S. Cl. ........................... 128/200.26; 128/207.14; 128/207.15
[58] Field of Search ................... 128/200.26, 207.14, 128/207.15, 657, 772; 604/95, 170

[56] References Cited

U.S. PATENT DOCUMENTS

| | | | |
|---|---|---|---|
| 2,498,692 | 2/1950 | Mains | 128/348 |
| 3,060,972 | 10/1962 | Sheldon | 138/120 |
| 3,416,531 | 12/1968 | Edwards | 128/348 |
| 3,521,620 | 7/1970 | Cook | 128/2.05 |
| 3,776,222 | 12/1973 | Smiddy | 604/95 |
| 3,802,440 | 4/1974 | Salem et al. | 128/772 |
| 3,968,800 | 7/1976 | Vilasi | 128/207.14 |
| 4,150,676 | 4/1979 | Jackson | 128/351 |
| 4,329,983 | 5/1982 | Fletcher | 128/207.14 |
| 4,502,482 | 3/1985 | DeLuccia, deceased et al. | 128/207.15 |
| 4,529,400 | 7/1985 | Scholten | 604/95 |
| 4,589,410 | 5/1986 | Miller | 128/207.15 |
| 4,685,457 | 8/1987 | Donenfeld | 128/207.14 |
| 4,690,138 | 9/1987 | Heyden | 128/207.15 |
| 4,846,153 | 7/1989 | Berci | 128/207.14 |
| 4,886,059 | 12/1989 | Weber | 128/207.15 |
| 4,886,067 | 12/1989 | Palermo | 128/657 |
| 4,949,716 | 8/1990 | Chenoweth | 128/207.14 |
| 5,058,577 | 10/1991 | Six | 128/207.14 |
| 5,235,970 | 8/1993 | Augustine | 128/207.14 |
| 5,259,377 | 11/1993 | Schroeder | 128/207.14 |
| 5,403,297 | 4/1995 | Imran | 128/657 |

*Primary Examiner*—Aaron J. Lewis
*Attorney, Agent, or Firm*—Eckert Seamans Cherin & Mellott

[57] ABSTRACT

A tool assists in placing an endotracheal tube into the trachea of a patient by controllable diverting of the end of the tube. A tool with at least one endmost link that can be manually diverted exclusively at the distal end using a lever handle, is placed in the tube. A proximal portion of the tool adjacent the handle at least partly defines an internal passage that can be an open channel. The proximal portion is substantially rigid, although it can be manually bent into a desired rigid arc. At least one distal link occupies 10–20% (4–5 cm) of the tool length and is attached to the proximal portion by a pivot pin permitting the distal link to pivot in the medial plane of the patient. The control member, namely a rod, wire or the like, passes anteriorly of the pivot pin relative to the patient, and is attached to the distal link. Tension applied to the control member diverts the end of the endotracheal tube by 90°–100°, for guidance through the larynx. The proximal portion is nearly as wide as the internal diameter of the endotracheal tube, which diverts to substantially the same extent as the distal link.

18 Claims, 5 Drawing Sheets

ENDOTRACHEAL INTUBATION APPARATUS

CROSS REFERENCE TO RELATED APPLICATION

This application is a continuation in part of application Ser. No. 08/187,609 filed Jan. 26, 1994, now abandoned.

BACKGROUND OF THE INVENTION

1. Field of the Invention

The invention relates to devices for assisting in oral tracheal intubation or placement of an endotracheal tube through the mouth, and in particular concerns an intubation guide approximating an internal diameter of the tube, the guide having a distal tip that is articulated and manually controlled to obtain a sharp anterior deflection at the end of the tube for passing the tube through the larynx.

2. Prior Art

Endotracheal tubes are used to couple a patient's respiratory system to a breathing apparatus during surgical procedures or emergency situations. A typical endotracheal tube is made of polyvinyl chloride or the like and has an inflatable cuff several centimeters from an end of the tube that is inserted into the trachea, whereby the tube can be sealed relative to the trachea by inflating the cuff through an inflation line passing along the tube. A fitting on an opposite end of the tube couples to an artificial respirator or ventilator.

The tube is dimensioned to provide an adequate airflow for the patient, and may have an internal diameter of 2.0 to 9.5 mm, depending on the air flow required, normally varying as a function of the size of the patient. A typical internal diameter for adults is 5.5 to 8.5 mm and a typical length is about 30 cm. The tube is somewhat flexible but must be sufficiently rigid to ensure that the lumen of the tube does not pinch shut or become restricted if the tube is flexed. Therefore, the tube has a substantial wall thickness to provide necessary rigidity, e.g. 2 mm wall thickness. The tube typically is manufactured to assume a smooth arc at rest, this arc approximating the curve of the passage through the mouth to the trachea. For example, from end to end the tube can define a quadrant (90°) of a circular arc with a radius of curvature of about 20 cm.

In placing the endotracheal tube, it is necessary to guide the cuffed or distal end of the tube around an anterior bend to bring the end of the tube forward through the larynx and into the trachea, rather than rearward into the esophagus and the digestive system. There are various situations in which the tube must be placed quickly, and in every case the tube must be placed properly so as to ensure airflow. In connection with surgery under general anesthesia, for example, a typical procedure is to render the patient unconscious, e.g., using pentothal, and also to administer a neuromuscular blocking agent such as succinylcholine to block involuntary and voluntary muscular movements that may interfere with a surgical procedure. This also stops respiration by disabling all muscles of respiration. At this point, the endotracheal tube must be properly positioned in a timely fashion to avoid potentially catastrophic results from hypoxia at the brain and heart. It is obviously desirable to place the tracheal tube properly on the first attempt.

Oral rather than nasal placement of the tracheal tube is generally preferred. Various tools have been devised to assist in placing the tube, i.e., threading the cuffed end through the mouth and the pharynx, turning forward to pass the epiglottis and larynx, and advancing the tube several centimeters into the trachea until the inflatable cuff passes the vocal cords. Typically, a laryngoscope having a generally spoon shaped blade is used to pull the tongue and associated tissues anteriorly (i.e., upwardly for a supine patient). Often, this is sufficient to enable proper placement of the endotracheal tube. Occasionally some form of tool is used to assist in guiding the tube into place.

According to one technique, a thin malleable metal stylette is inserted into the trachea for guiding the tracheal tube into place by sliding the tube along the stylette. First the stylette is bent manually to approximate an estimated path of the tracheal tube, i.e., the stylette is curved into an arc and may be diverted or bent anteriorly at the distal end so as to point toward the larynx when inserted orally. The length and extent of the bend that is possible is limited by the need to pass the stylette along the path to the trachea. The endotracheal tube is placed on the stylette, which is inserted into the patient. The tube then is pushed axially along the stylette, and if all goes well, into the trachea. This approach requires correct estimation of the path and a certain dexterity, and sometimes requires repeated attempts as the stylette is adjusted, tried, removed and adjusted again.

The stylette has a substantially smaller diameter than the tracheal tube. Although the stylette may traverse the larynx, the end of the tube, which is wider, may encounter tissues and require repositioning to enable the tube to pass. Additionally, because the stylette is thin compared to the inside diameter of the tube, the tube does not bend to the same angle as the stylette and instead assumes a longer radius of curvature. The stylette is inexpensive, but it is a cumbersome, time consuming and inefficient means to achieve a bend at the distal tip of the endotracheal tube for guiding the tube into place.

A stylette including a mechanism for manually varying a bending arc at the distal end of the stylette, is available from Mainline Medical, Inc., Smyrna, Ga., under the name Flexguide. The stylette is made of flexible plastic, laterally slotted exclusively along one side to define a series of articulated segments over a span of several centimeters at the distal end portion of the stylette. A solid movable plunger extends axially through a central passageway and is attached or abutted against a segment at the distal end. By pulling or pushing the plunger relative to the remainder of the stylette using a finger ring, the distal end is caused to bend toward or away from the slotted side, respectively. Due to the segment structure, bending occurs evenly over the span of segments, such that it is difficult to make an abrupt bend. The stylette is also narrow compared to the internal diameter of the endotracheal tube, making it difficult or impossible to use the tool to alter the curve of a tube placed on the stylette. Instead, diversion of the end of the stylette is used to aim the end of the stylette toward the larynx, using the four or five centimeters of tissue space in the area of the pharynx and larynx. The stylette is placed in the trachea and the tube is pushed along the stylette in the same manner as with a malleable metal stylette.

Other devices are known that are intended to bend the endotracheal tube itself. In U.S. Pat. No. 4,329,983—Fletcher, a stylette is coupled to a wire to enable the distal end of the stylette to be pulled into an arc when inside the lumen of the tube. Whereas the stylette is thin compared to the tube, the stylette must be bent into a relatively sharper curve in order to form a relatively more shallow curve in the tube. In U.S. Pat. Nos. 4,589,410—Miller and 4,150,676—Jackson, pull rings at the proximal end are tied to the distal end via a wire or the like disposed in a passage on one side of the tube. Pulling the ring shortens that side of the tube and increases the bend toward the side. In U.S. Pat. No. 4,685, 457—Donenfeld, several wires and passages are provided for bending the tube in different directions by manipulation using the proximal end of the tube. In each of these wire-in-passage arrangements, the bend occurs smoothly along the entire length of the tube toward the side that is shortened. Thus, the tube is pulled into a tighter arc than the nominal arc in which the tube is supplied, and accordingly bears laterally against tissues in the mouth and/or throat.

In certain instances, a smooth bend in the tube is insufficient to guide the tube into the larynx and trachea. Patients having a small receding chin (micrognathia), an unusually anterior larynx, or a relatively short, thick neck may present problems because although the patient's head may be tilted back, the passage into the larynx still requires a sharp anterior bend. In certain trauma victims, it may be unwise to tilt the head to extend the neck for straightening the path of the endotracheal tube.

In U.S. Pat. No. 4,529,400—Scholten, a similar tool is provided for bending an endotracheal tube. A plurality of articulated links are arranged in a flexible plastic tube, from an area near a handle at the proximal end to a link at the distal end. A wire is coupled from the handle to the endmost distal link. All of the links exclusively pivot in one direction, but a second link from the distal end is arranged to permit a pivot in only the opposite direction. Generally, the device pulls the length of the tool into a tighter curve in one direction only, namely anteriorly, and the tool bends continuously over its length in a manner similar to the wire-in-passage devices discussed above. However, the second link from the distal end cause a diversion in the opposite direction. Thus, the Scholten tool is useful for nasotracheal intubation in that the continuous bending of the proximal links applies force to push the soft palette and epiglottis anteriorly, guiding the tube toward the larynx in a generally circular bend, whereas the distal link is diverted posteriorly in an S-shaped bend, such that the distal end of the tube passes through the vocal cords along a line perpendicular to the extension of the vocal cords. The device is particularly adapted for nasotracheal intubation due to its S-shaped bend. The arrangement of links along its full length is expensive.

Continuously bending tool arrangements generally cannot follow the anatomy as needed for oral intubation because the tube bends generally along its length. The tube is supplied in the nominally expected arc of the passage from mouth to larynx, and it is the distal end of the tube that needs to bend to pass the larynx generally perpendicular to the vocal cords. General bending to a shorter radius arc may cause the distal end to move closer to the direction of tracheal insertion, but may not bring the distal end into a position needed for passage into particularly anterior tracheal openings. If the bend is increased, such tools apply force to portions of the patient's anatomy in a direction laterally of the tube, and are not fully adequate for guiding the end of the endotracheal tube into place. It would be advantageous to improve intubation techniques by providing an intubation assist tool that follows the pattern of the patient's anatomy rather than applying force, that uses the tube itself as the insertion device instead of a stylette along which the tube slides, and that can be diverted at the distal end by a substantial angle as needed for oral intubation in difficult circumstances. It would also be advantageous to provide a means to assist in intubation in real time, by enabling diversion of the end of the tube to a precise angle while under direct visualization, in a non-cumbersome fashion and without applying force to surrounding oropharyngeal structures.

SUMMARY OF THE INVENTION

It is an object of the invention to provide an intubation assist tool that fits closely to the inner diameter of an endotracheal tube such that bending of the tool produces closely corresponding bending of the tube.

It is another object of the invention to employ a generally rigid endotracheal tube guide, formed generally into a fixed arc, and that has a mechanism for manually controlled additional bending exclusively adjacent the distal end.

It is also an object of the invention to provide an ergonomic oral intubation assist tool that conforms to the user for operation with one hand while using the other hand to manipulate a laryngoscope.

It is another object of the invention to provide an intubation assist tool that is useful for normal and abnormal anatomies, and which is durable and inexpensive.

It is still another object to manipulate the distal end of an endotracheal tube to a precisely correct angle in real time (i.e., without withdrawing the endotracheal tube from the mouth), under direct visualization, thereby obtaining the full advantage of the dexterity of the operator in placing such tubes in patients having varying anatomies.

These and other objects are accomplished by a tool that assists in oral placement of an endotracheal tube in a patient and has an elongated proximal portion with an internal passage, defining a fixed arc corresponding to the passage through the mouth to the larynx, i.e., arching anteriorly in a medial plane of the patient toward a distal end of the tool.

In one embodiment of the invention, two links occupy 10-20% (4-5 cm) of the tool length and are attached to the proximal portion by pivot pins permitting the links to pivot in the medial plane. A control line, which can comprise a flexible wire, extends through the proximal portion, passing anteriorly of the pivot pins, and is attached to the endmost link. Tension applied to the control line by a lever diverts the links exclusively anteriorly of the fixed arc, thereby diverting the end of the endotracheal tube at least 90°–100°, for guidance through the larynx. The proximal portion is nearly as wide as the internal diameter of the endotracheal tube, which diverts to substantially the same extent as the links.

In another embodiment, the tool has a single link. The link occupies 10-20% (4-5 cm) of the tool length. The link is attached to the proximal portion of the tool by a pivot pin such that the link can pivot in the medial plane. A control line extends through the proximal portion of the tool, and preferably comprises an elongated rod such as a solid but flexible length of stainless steel. The control line attaches anteriorly of the pivot pin to the link at a pivot coupling. When tension is applied to the control line by a lever at the proximal end of the tool, the link pivots anteriorly of the fixed arc, producing a sharp bend at the distal end of the endotracheal tube and facilitating guidance of the tube through the larynx and into the trachea. As with the two link embodiment with the wire control line, the outer diameter of the proximal portion and the link is nearly as large as the inside diameter of the endotracheal tube. Thus the tube is diverted to substantially the same extent as the link, e.g., approaching 90° relative to a longitudinal axis of the tool adjacent the distal end.

The intubation assist apparatus is user friendly in that no new skill, knowledge or dexterity must be learned in order to use it. The laryngoscope blade and endotracheal tube can be inserted into the mouth in a conventional manner. Once inserted, and with the intubation assist apparatus in place, the endotracheal tube and laryngoscope remain in place and need not be withdrawn for adjustments. The distal end of the endotracheal tube is controllably diverted by manual action of the operator in real time, under direct visualization, making it readily possible to obtain the angle necessary and to negotiate the bend from the posterior oropharynx into the trachea.

Once the endotracheal tube is properly inserted, the intubation assist apparatus is readily removed from the tube because upon release of manual pressure on the control lever by the operator, pressure on the inside of the endotracheal tube is released, and the intubation assist apparatus relaxes into the unidirectional bend defined by the endotracheal tube. No pressure or force need be exerted on the surrounding pharyngeal structures in order to cause the endotracheal tube and the intubation assist apparatus therein to negotiate the necessary curve.

BRIEF DESCRIPTION OF THE DRAWINGS

There are shown in the drawings certain exemplary embodiments of the invention as presently preferred. It should be understood that the invention is not limited to the embodiments disclosed as examples, and is capable of variation within the scope of the appended claims. In the drawings.

DETAILED DESCRIPTION OF THE PREFERRED EMBODIMENTS

Figure 1:
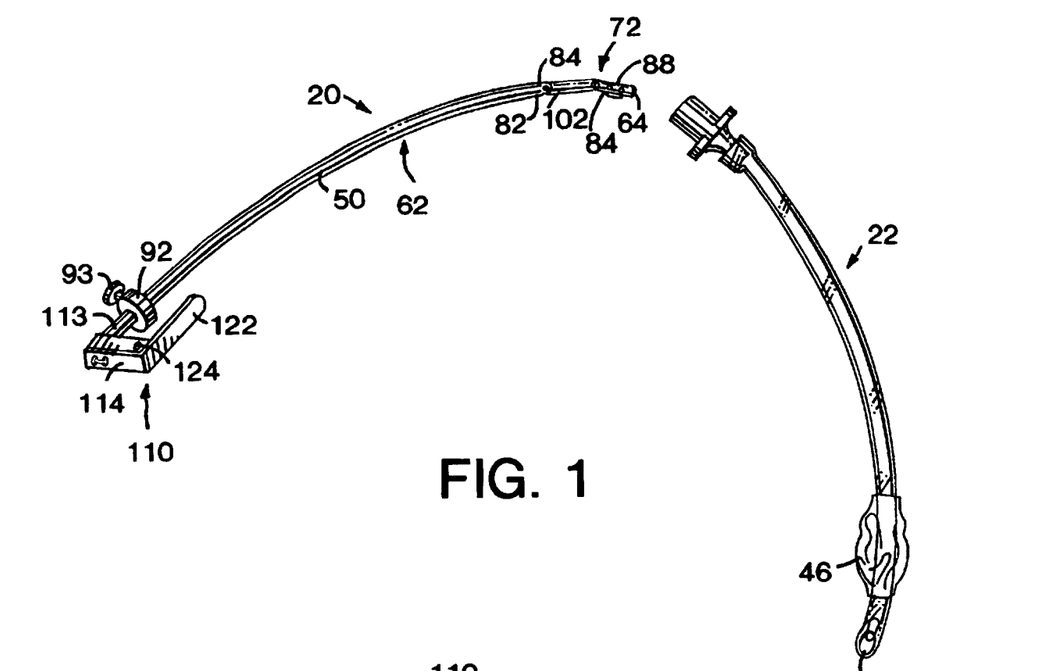
FIG. 1 is a perspective view illustrating the tool for assisting in manual placement of an endotracheal tube in a patient, the tube and the tool being shown arranged for insertion of the tool into the tube.
Figure 2:
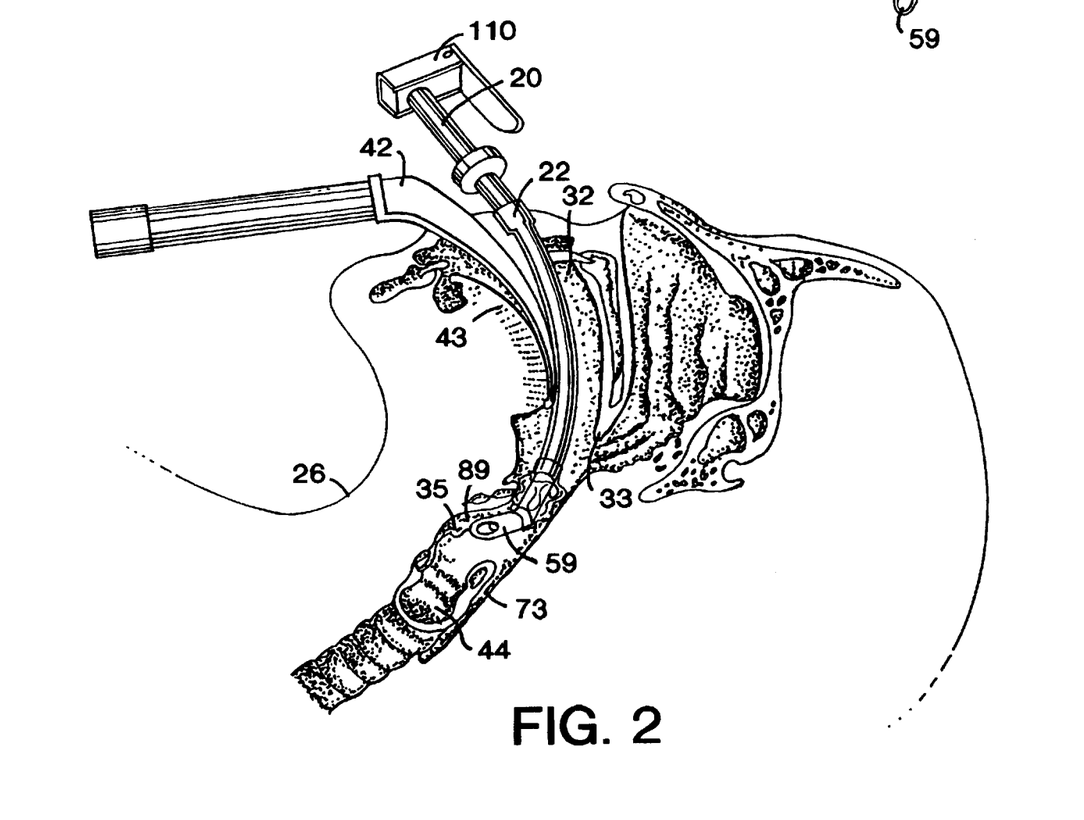
FIG. 2 is a partial section view along the medial plane of a human, demonstrating use of the tool together with a laryngoscope.

A tool 20 for assisting in manual placement of an endotracheal tube 22 in a patient 26 is shown in FIGS. 1 and 2. Tool 20 is placed inside endotracheal tube 22 as shown in FIG. 1, being simply slipped into the lumen of tube 22, where the tool occupies a substantial proportion of the internal diameter of the tube. For intubation, tube 22 is passed, with tool 20 therein, along a route through the patient's mouth 32, pharynx 33 and larynx 35, as shown in FIG. 2, preferably with the aid of a laryngoscope 42 for lifting the tissues of the tongue 43 and enabling viewing of the area at the rear of the throat in the area of the larynx 35. Tube 22 is advanced through larynx 35 into trachea 44 until an inflatable cuff 46 passes the vocal cords. By use of tool 20, tube 22 is diverted anteriorly at its end, to assist in insertion through larynx 35 and into trachea 44.

Tool 20 includes an elongated proximal portion 50 with an internal passage 52 through which a control member 55 passes as described in more detail below, for controlling bending of tube 22, and more particularly for forming a relatively sharp anterior bend at a distal end 59 of tube 22 over a limited distance, for example about 1 to 5 cm. In the embodiment of FIG. 1, proximal portion 50 is a continuous length of relatively rigid tubing, forming a bend in a fixed arc 62, leading to a distal portion 64 at which an articulated link mechanism 72 is mounted so as to allow bending of a distal portion of tube 22 anteriorly of the patient as needed to pass end 59 of endotracheal tube 22 forward of the esophagus 73 and into trachea 44. Control member 55 in this embodiment is a flexible line such as a wire or chain, conveying tension to one or more pivotable end segments to divert the end of the tool.

As shown in FIGS. 1–4, proximal portion 50 defines an arc corresponding to the route through mouth 32 to the area of larynx 35, and extends anteriorly in a medial plane 77 of patient 26 toward distal end 64 of tool 20. The fixed arc is thus shaped, and proximal portion 50 is sufficiently long to position tube 22 adjacent larynx 35. However, a tangent to the fixed arc may be aligned more to esophagus 73 than trachea 35, particularly in patients having a very anterior larynx.

At least one articulated link 88, and a plurality of articulated links in FIGS. 1–4, are pivotally attached to proximal portion 50 at its distal end 82 by a respective pivot pin 84 permitting link 88 to pivot relative to proximal portion 50 in the patient's medial plane 77 and in particular to divert distal end 64 of tool 20, and endotracheal tube 22 thereon, anteriorly by manual action of the user.

Elongated control member 55 extends through the bore or passage 52 along the length of proximal portion 50. Control member 55 passes anteriorly of pivot pin 84 and is attached to distal link 88. Accordingly, when tension is applied to control line 55, distal link 88 is diverted anteriorly relative to a tangent of fixed arc 62 in medial plane 77, thereby diverting endotracheal tube 22 for guidance through larynx 35. Distal end 59 of endotracheal tube 22 is diverted anteriorly so as to become aligned substantially perpendicular to the extension of the vocal cords 89, whereupon endotracheal tube 22 can be advanced into trachea 44 by further manual advance of tool 20 and tube 22 thereon.

The distal link portion 64 of tool 20, and preferably both proximal and distal portions 50, 64 have an outside diameter that is substantial relative to the inside diameter of tube 22. Accordingly, the arc 62 and a diversion angle achieved by tool 20 are substantially achieved in tube 22 as well. The outside diameter can be equal to 50 to 90% of an internal diameter of endotracheal tube 22, typically 2.0 to 9.5 mm, and in particular 5.5 to 8.5 mm for intubation of an adult. The proximal and distal portions 50, 64 preferably have an outside diameter approximating an internal diameter of endotracheal tube 22, with sufficient clearance to permit free sliding of tool 20 in endotracheal tube 22 for easy withdrawal of tool 20 after tube 22 has been placed. In this manner, endotracheal tube 22 is diverted substantially to a same extent as the at least one link 88.

Tool 20 is preferably only slightly longer than tube 22, which typically is about 30 cm in length. However, as a means to position distal end 64 of tool 20 precisely at the distal end of tube 22, a stop ring 92 and thumbscrew 93 can be provided as shown in FIG. 1. Stop ring 92 can be positioned as required along proximal portion 50 of tool 20 and locked in place by tightening thumbscrew 93.

In one embodiment of the invention, shown in FIGS. 1–9, a plurality of links 88, 102 are provided at distal end 64 of tool 20, attached to proximal portion 50 by pivot pins 84 coupling links 88, 102 together serially and with proximal portion 50, and the connecting member comprises a length of thin flexible wire or the like. Each pivot pin 84 permits a respective one of links 88, 102 to pivot anteriorly in the medial plane described by the fixed arc of proximal portion 50.

Figure 3:
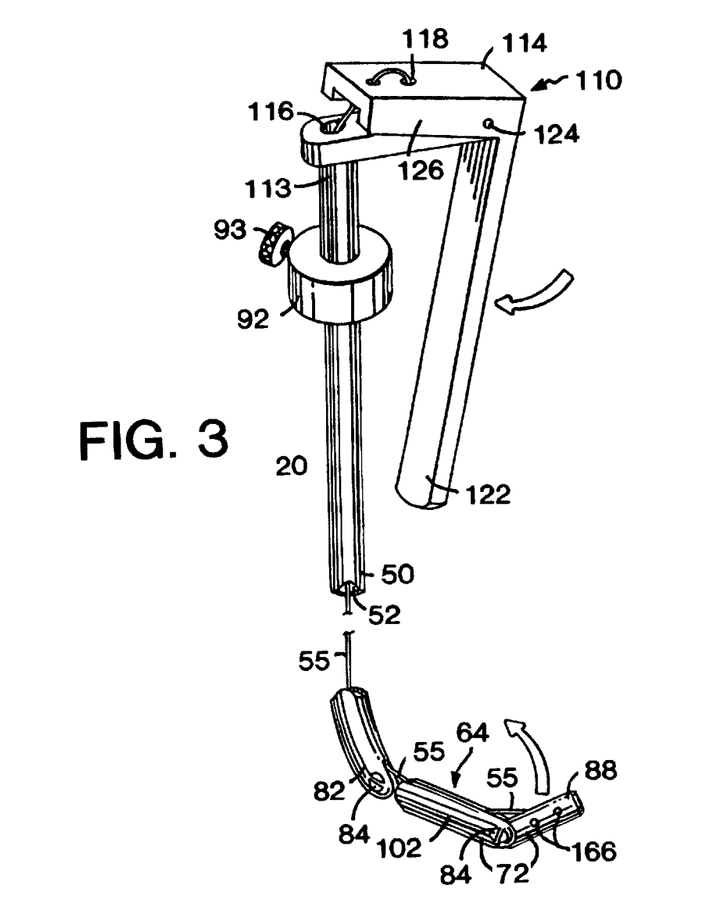
FIG. 3 is a perspective view of the tool showing the proximal and distal end portions, the tool shown cut away between the end portions.

In FIG. 3, proximal portion 50 is shown cut away to better illustrate pivoting links 88, 102 at distal end 64 of tool 20 and the details of a handle 110 whereby tension is applied to control member 55 for diverting links 88, 102 anteriorly of the arc 62 defined by proximal portion 50. Links 88, 102 are diverted by tension on control member or line 55 in part because the control line passes anteriorly of each of the pivot pins 84. Thus links 88, 102 all pivot in a same direction, namely anteriorly in medial plane 77, as tension on control line 55 shortens the distance on the anterior side of tool 20, between proximal portion 50 and the endmost distal link 88.

The pivoting links 88, 102 extend only over a short distal length, for causing the end of endotracheal tube 22 to divert toward larynx 35 and trachea 44. Preferably, the pivoting portion 72 defined by links 88, 102 extends about 10 to 20% of the length of tool 20, which enables a substantial bend or diversion to be formed at the distal end of tube 22. Proximal portion 50 is rigidly curved in fixed arc 62 and is not displaced during diversion of distal links 88, 102. Proximal portion 50 can be permanently formed into the fixed arc or can be slightly malleable such that fixed arc 62 can be changed by manually bending proximal portion 50. Preferably, proximal portion 50 is bendable only with difficulty, if at all, and consists substantially of an integral rigid tube of stainless steel or relatively rigid plastic.

Figure 4:
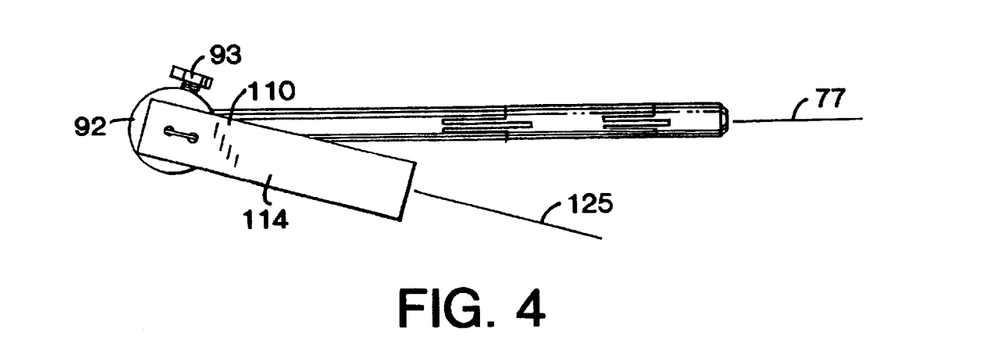
FIG. 4 is a top plan view of a preferred embodiment, showing the alignment of the handle to the plane in which the elongated portion of the tool bends.

Referring to FIGS. 3 and 4, one means for applying tension to control line 55 includes handle means 110 having a base 112 at a proximal end 113 of proximal section 50 and a lever 114 pivotally mounted on base 112. Control line 55 is attached to lever 114 for application of tension to control line 55 by pulling upward (in FIG. 3) on the control line or member relative to base 112. Base 112 can be a metal block with a hole 116 for receiving proximal portion 50 via press-fitting, and permitting control line 55 to pass to a point of attachment 118 on lever 114. Lever 114 in this embodiment has a paddle portion 122 pivoted to base 112 at a pivot pin 124 spaced from proximal portion 50. Therefore, by pivoting paddle portion 122 toward the base or toward proximal portion 50, point of attachment 118 of control line 55 is lifted, applying tension to the control line and diverting distal links 88, 102.

In FIG. 4, proximal portion 50 and its fixed arc or bend 62, and also the pivot path of links 88, 102, each reside in a horizontal plane, which is the medial plane of patient 26 when tool 20 is in use. However, the plane 125 including paddle portion 122 of lever 114 is angled approximately 15% relative to the medial plane. This is an ergonomic arrangement for manual handling of tool 20. In FIG. 4, paddle 122 is angled about 15° downward or clockwise from the medial plane, which is comfortable for a user who manipulates tool 20 with his or her right hand. Paddle 122 can be angled in the opposite direction for persons who prefer to manipulate tool 20 with the left hand, e.g., left-handed people or right handed people who prefer to use the right hand to manipulate laryngoscope 42 as in FIG. 2.

As best shown in FIG. 3, lever 114 has an L-shape, with paddle portion 122 and a base leg 126 forming the L-shape. Lever pivot pin 124 extends through base leg 126 at a point spaced from internal passage 52 of proximal portion 50 and control line 55 being attached to base leg 126. The lever can be arranged such that paddle portion 122 and base leg 126 are perpendicular (i.e., with the paddle portion parallel to proximal portion 50 at rest), or for additional clearance the paddle portion can be over 90° relative to the base leg to allow a greater range of movement of the lever until paddle 122 contacts proximal portion 50.

FIG. 3 also shows stop 92 on proximal portion 50 and thumbscrew 93 or similar means provided for adjusting and fixing stop 92 at a desired longitudinal position along proximal portion 50. Stop 92 is wider than the internal diameter of tube 22, and when tube 22 is pushed upwardly against stop 92, e.g., as shown in FIG. 2, the pivotal links 88, 102 at the distal end of endotracheal tube 22 reside inside tube 22 closely adjacent the end tube 22. Tool 20 thus remains inside tube 22, but is operative to divert the end of tube 22 anteriorly. For a shorter tube 22, stop 92 is adjusted downwardly, etc.

FIGS. 3–8 illustrate aspects of preferred pivotal links 88, 102 at distal end 64 of tool 20. At least one link is articulated at distal end 64, and preferably a plurality of links are provided, extending four or five centimeters from the extreme distal end. Links 88, 102 are articulated via pivot pins formed by screws 132, providing a durable arrangement that allows the user to exert the necessary pressure on tube 22 from inside, along a limited length at distal end 64. Two links are provided in the preferred arrangement shown. A more proximal intermediate link 102 is attached to proximal portion 50 at its distal end by a first pivot pin 84. An endmost distal link 88 is attached to the proximal or intermediate link 102 by a second pivot pin 84, parallel to the first pivot pin. Whereas the nature of the respective articulation joints is the same, the same reference numbers are used to identify corresponding parts of each. Control line 55 passes on an anterior side of each of the first and second pivot pins 84.

Figure 5:
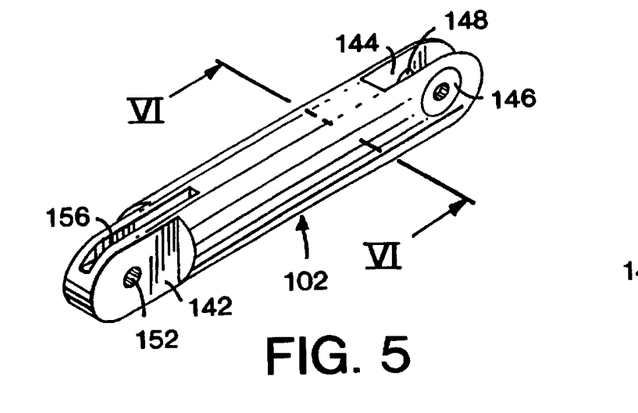
FIG. 5 is a perspective view illustrating an intermediate link between a distal link and the elongated portion of the tool.

FIG. 5 shows a preferred arrangement of intermediate or proximal link 102. First end 142 of proximal link 102 has a narrowed shape due to chordal flattening on opposite lateral sides for a distance adjacent first end 142, parallel to the medial plane. As shown in FIG. 1, a clevis or U-shaped slot 144 in a lower end of proximal portion 50 receives the narrowed first end 142 of proximal link 102. The clevis 144 has a depression 146 such as a counterbore (for a machine screw) or countersink (for a flat head screw) for receiving the screw 132 that functions as pivot pin 84. The screw head lies flat on one side of clevis 144 and engages a threaded hole 148 on the other side. A through bore 152 in first end 142 of link 102 allows screw 132 to pass through and enables link 102 to pivot. Distal link 88 similarly has a narrowed end 142 for engaging a clevis 144 in the more proximal link 102.

Figure 6:
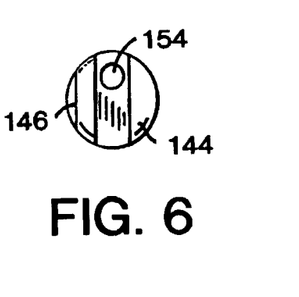
FIG. 6 is an elevation view along line 6—6 in FIG. 5.

Preferably, clearance is provided for control member 55, in this case a flexible line, in a manner that permits the line 55 to become displaced from pivot pin 84 when link 88 or 102 is diverted. Control line 55 passes through an off-center longitudinal bore 154 through a body of link 102, as shown in FIG. 6. A lateral slot 156 communicating with off-center bore 154 extends toward the adjacent link 88 along the anterior side of male end 142 of each of the clevis fittings. On the female ends of the clevis fittings, the U-shaped slot 144 can be made slightly longer longitudinally than is needed for clearance with the corresponding male end 142 of the adjacent part of the clevis fitting, also providing clearance for control line 50. The result is illustrated in FIG. 1. When links 88, 102 are diverted by tension on control line 55, clearance provided by lateral slots 156, and preferably also by the depth of U-shaped slots 144, permit control line 55 to move anteriorly. A sharp distal bend or diversion is thus obtained at the end 64 or tool 20, and in tube 22 carried thereon.

Figure 7:
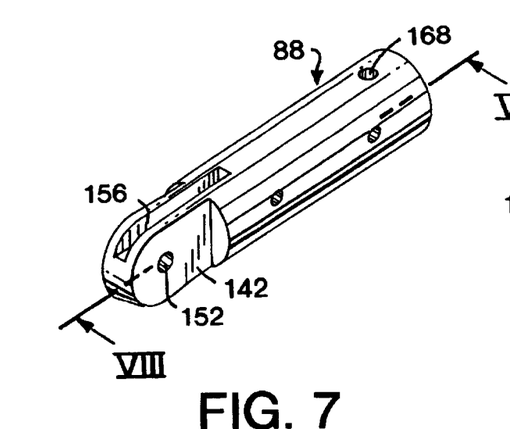
FIG. 7 is a perspective view illustrating the distal link.
Figure 8:
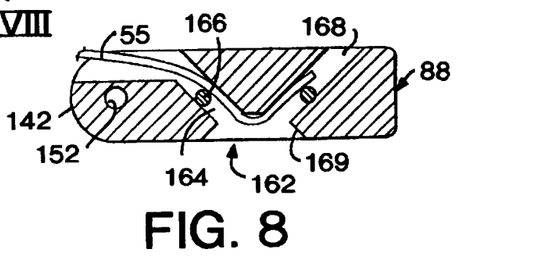
FIG. 8 is a section view along lines 8—8 in FIG. 7, with the control line also being shown.

Referring to FIG. 7, distal link 88 preferably articulates on intermediate link 102 via the same form of structure as used for articulating intermediate link 102 to proximal portion 50. However, control line 55 attaches to distal link 88 at a point spaced longitudinally from pivot pin bore 152, rather than movably passing through an off-center bore 154 as with link 102. In the embodiment shown, a first longitudinally-inclined transverse bore 164 is provided at an end of lateral slot 156 of link 88. A set screw 166 (shown in FIG. 1 but not FIG. 8) engages control line 55 in transverse bore 164 to affix control member 55 to distal link 88. Preferably, a second transverse bore 168 inclined in an opposite longitudinal direction is provided with a similar set screw means for attaching the extreme end of the control line to distal link. Second bore 168 and its set screw 166 provide additional security of connection. Due to the passage of control line 55 around an angle between the transverse bores, control line 55 is affixed securely and permanently. A shallow slot 169 can be provided in a surface of link 88 between transverse bores 164, 168, such that control member 55 remains inside the outer contour of distal link 88. Control member 55 can be attached to handle lever 114 in the same manner.

In the exemplary embodiment shown, and for an adult size endotracheal tube, links 88, 102 and proximal portion 50 are about 5 mm in diameter, or 0.6 to 0.75 of the internal diameter of tube 22. Intermediate link 102 is about 3 cm long; distal link 88 is about 2.3 cm; lateral slot 156 is about 1 cm long; and U-shaped slots 144 of the clevis fittings are about 2 mm deeper (longitudinally) than needed for clearance with narrowed ends 142. According to these dimensions, the two serially coupled links 88, 102 can divert endotracheal tube 22 from a neutral position along a tangent of fixed arc 62 to a diverted position wherein the extreme end of endotracheal tube 22 is angled at least 90° to 100° anterior of said tangent.

Another embodiment of the invention is shown in FIGS. 10–17, using the same reference numbers to identify corresponding structural parts. In the embodiment shown in FIG. 10, a single distal link 88 is provided at distal end 64 of tool 20, attached to proximal portion 50 by pivot pin 84 coupling distal link 88 with proximal portion 50, and the tool can otherwise be as described above. Pivot pin 84 permits distal link 88 to pivot anteriorly in medial plane 77 relative to proximal portion 50. This bends the tube exclusively at the distal end, and proximal portion 50 remains fixed in shape.

Figure 11:
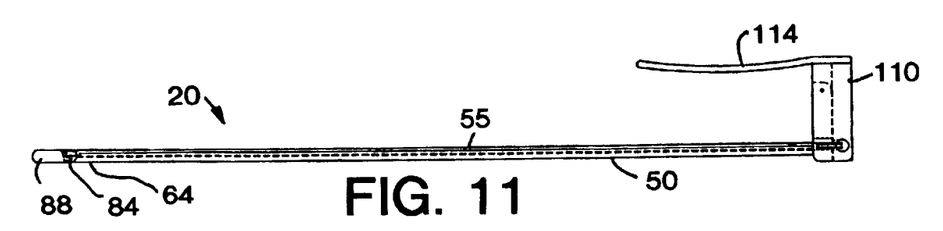
FIG. 11 is an elevation view of another alternative embodiment of the tool, having a rod and channel structure and one movable segment.
Figure 12:
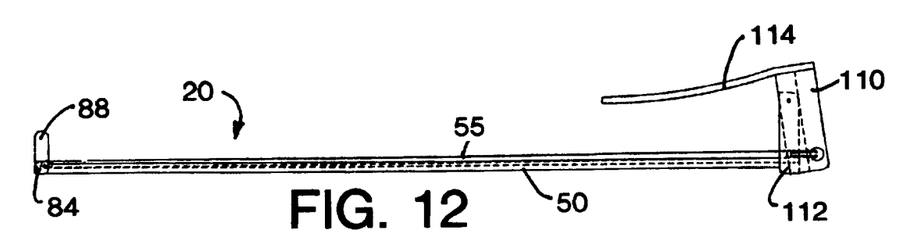
FIG. 12 is an elevation view of the embodiment according to FIG. 11, with the movable segment shown in its extreme deflected position.

In a preferred embodiment shown in FIGS. 10–17, control member 55 comprises a solid elongated rod of stainless steel or the like, received in a channel along proximal portion 50 and attached to the lever handle at one end and to link 88 at the other end. The pivot axis of the connection between link 88 and control member or rod 55 is laterally displaced from the pivot axis of pin 84, connecting link 88 to proximal member 50. Therefore, from an undiverted position as shown in FIG. 11, tension on control rod 55 applied by handle 110 causes link 88 to divert as shown in FIG. 12.

Figure 13:
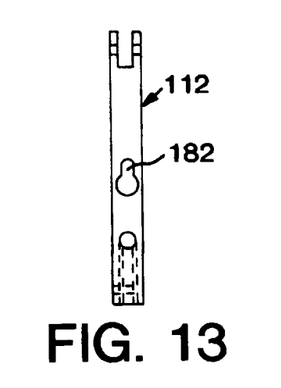
FIG. 13 is an elevation view showing a preferred base member for the tool according to FIGS. 11 and 12.

Proximal portion 50 in this embodiment is rigid as in FIGS. 1–10, but is shown substantially straight. The proximal portion 50 could also be somewhat curved, however the pivoting connection with handle 110 is such that longitudinal displacement of control rod 55 relative to proximal portion 50 causes lateral displacement of rod 55 upwardly or downwardly in the channel along the side of proximal portion 50, particularly near handle 110. Control member 55 is threaded at the handle end and coupled to a threaded cylindrical plug in a bore in the handle. As shown in FIG. 13, the stationary base of handle 110 has a clearance opening 182 permitting longitudinal and lateral movement of control member 55 therein.

Figure 14:
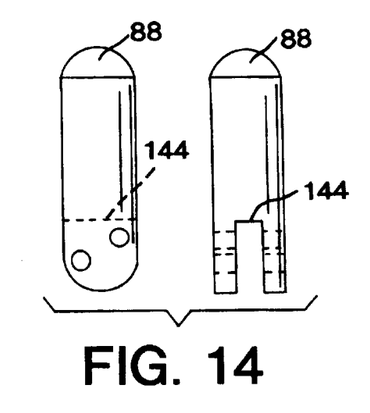
FIG. 14 shows side and end elevation views of the movable segment.

The laterally spaced pivot connections between link 88 and proximal portion 50 as well as control rod 55, can be made using screws, press-fit pins or rivets (not shown). FIG. 14 shows the shape of link 88 in side view as in FIGS. 11 and 12, and in a top view. Link 88 is generally cylindrical with a rounded distal end and a proximal end having a slot receiving the narrowed ends of members 50 and 55. The pivot pins are fixed in laterally spaced transverse holes in the slotted end, passing through clearance holes in members 50, 55 for pivoting.

Figure 15:
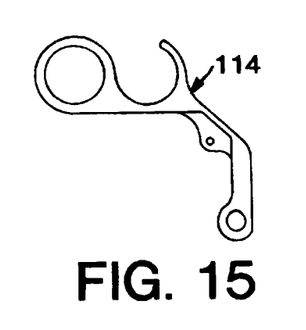
FIG. 15 is an elevation view showing an alternative structure for the lever handle of the tool.
Figure 16:
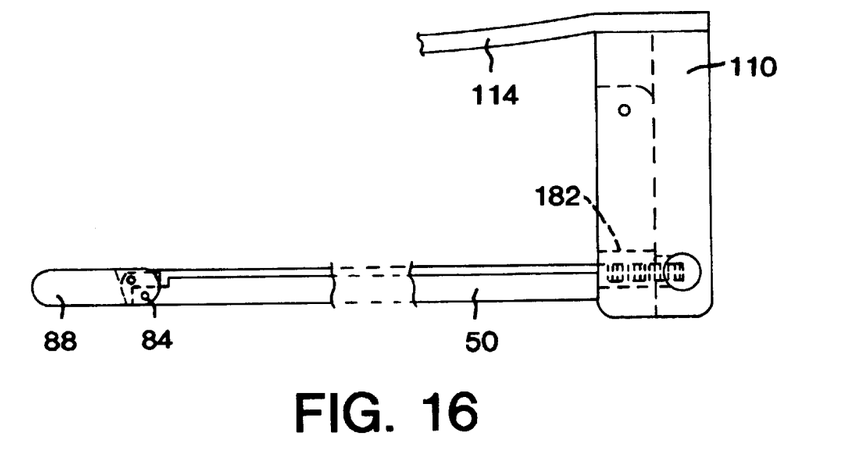
FIG. 16 is a partly cut-away elevation view corresponding to FIG. 11, showing the movable segment and lever handle positions with the segment undeflected.
Figure 17:
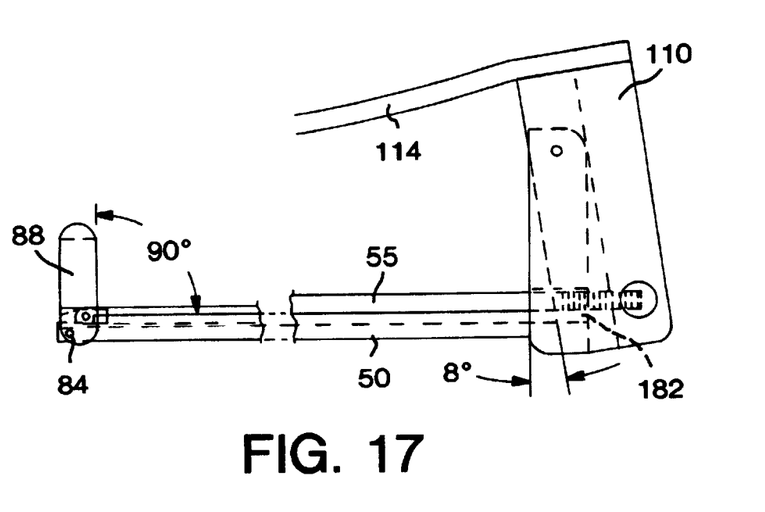
FIG. 17 is a partly cut-away elevation view corresponding to FIG. 12, showing the movable segment and lever handle positions with the segment deflected to a maximum of 90°.

An alternative form of lever for handle 110 is shown in FIG. 15, and employs finger openings instead of a straight lever handle as in FIGS. 11 and 12. The finger openings can include a closed ring enabling the operator to exert tension to divert link 88 or compression to bring link 88 back into alignment with proximal portion 50. However, in general the endotracheal tube 22 (see FIGS. 1 and 2), which is relatively thick and springy to avoid pinching off the lumen of the tube, tends to urge link 88 toward a position of alignment with proximal portion 50.

The embodiment of FIGS. 11–17 is more durable than an arrangement in which control member 55 is a flexible wire. A flexible wire control line is subject to metal fatigue at the connections with handle 110 and link 88, where the wire is repeatedly flexed in using the tool. A flexible wire as in the embodiments of FIGS. 1–10 also has a tendency to wear against the inside edges of proximal member 50 and link(s) 88. The embodiment of FIGS. 11–17 does not suffer from this type of wear.

Distal link 88 extends only over a short distal length, for causing the end of endotracheal tube 22 to divert toward larynx 35 and trachea 44. In FIGS. 11–17, for example, link 88 can be about 6 mm (0.25 inch) in diameter. Link 88 can be diverted from a position of alignment with proximal portion 50 (FIG. 16) to about 90° diversion (FIG. 17) by diverting the lever handle by about 8°. Preferably, distal link 88 extends only a limited distance along the length of tool 20, protruding for example by 13 mm (0.5 inch) in FIG. 17. This allows a substantial controllable bend or diversion to be formed at the distal end of tube 22, particularly because the tool occupies a large part of the internal diameter of tube 22.

In the exemplary embodiment shown, and for an adult size endotracheal tube, distal link 88 and proximal portion 50 are about 5 mm in diameter, or 0.6 to 0.75 of the internal diameter of tube 22. Distal link 88 is about 5 cm; and the U-shaped slot 144 on the distal end is about 2 mm deeper (longitudinally) than needed for clearance with narrowed end 142 of distal link 88. According to these dimensions, distal link 88 can divert endotracheal tube 22 from a neutral aligned position to a diverted position wherein the extreme end of endotracheal tube 22 is angled by substantially 90° anteriorly of the longitudinal axis of proximal portion 50.

Both of the above embodiments are very effective for inserting tube 22 through larynx 35, and are effective even for patients having potential problem anatomies or conditions, such as an unusually anterior larynx, short chin or trauma that limits freedom to tilt back the head. Of course other specific dimensions and specific articulation structures are also possible.

Figure 9:
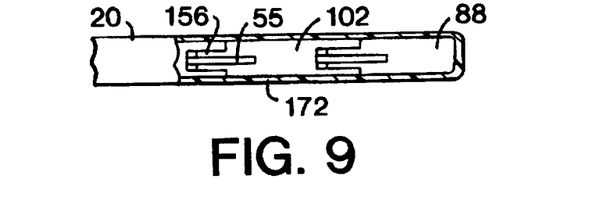
FIG. 9 is a partial elevation view illustrating an antifriction covering on the tool.
Figure 10:
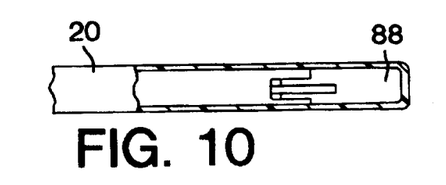
FIG. 10 is a partial section view illustrating a further embodiment of the tool according to FIGS. 1–9, having a single movable end segment.

Proximal portion 50 and the link or links 88 define a generally smooth cylindrical outer contour. The respective parts are preferably made of a surgical stainless steel. An antifriction covering such as polytetrafluoroethylene (Teflon) can be provided as shown in FIG. 9, or the parts can be bare stainless steel as appropriate for autoclaving.

It is possible to include a spring (not shown) providing a bias tending to urge the lever handle in a direction opposite the direction that places tension on control member 55. For example, a compression spring can urge the paddle 122 of lever handle 112 outwardly from handle base 112, opposed by the user's grasp. However, it has been found that the inherent stiffness of endotracheal tube 22 is sufficient to provide a return force for bringing links 88, 102 back to their rest position when tension on control line 55 is released, and allowing tool 20 to be withdrawn quickly and easily from tube 22.

The dimensions of tool 20, the angle to which links 88, 102 can be diverted and other aspects of the invention can be varied as needed for particular circumstances, e.g., smaller or larger tracheal tubes and/or patients, use for patients having a normal-anatomy vs. an unusually anterior larynx. The invention is convenient and useful with normal anatomies, as well as being particularly useful for those anatomies in which intubation problems are otherwise encountered.

The invention having been disclosed in connection with the foregoing variations and examples, additional variations will now be apparent to persons skilled in the art. The invention is not intended to be limited to the variations specifically mentioned, and accordingly reference should be made to the appended claims rather than the foregoing discussion of preferred examples, to assess the scope of the invention in which exclusive rights are claimed.

We claim:

1. A tool for assisting in manual placement of an endotracheal tube in a patient such that such an endotracheal tube passes through a mouth, pharynx and larynx of the patient, the tool comprising:

an elongated proximal portion at least partly defining a fixed arc and passage leading toward an articulating distal end of the tool, the proximal portion being substantially rigid;

at least one articulating distal link attached to the distal end of the proximal portion of the tool by at least one pivot pin defining a pivot axis perpendicular to a plane occupied by the proximal portion, thereby permitting the link to pivot relative to the proximal portion in said plane;

an elongated control member extending along the passage and being attached to the distal link, the control member being laterally spaced from the pivot axis in said plane;

means for applying tension to the control member such that an articulating distal link portion is diverted relative to the fixed arc of the substantially rigid proximal portion toward said inner side of the pivot axis in the plane; and, wherein the proximal portion is substantially integrally rigid, whereby the endotracheal tube can be diverted substantially exclusively at the link toward said inner side to achieve said manual placement.

2. The tool according to claim 1, wherein the articulating distal link extends only over a distal length of about 10–20% of a length of the tool.

3. The tool according to claim 1, wherein the articulating distal link encompasses a length of about 4–5 cm of the tool.

4. The tool according to claim 1, wherein the proximal portion and the articulating distal link comprise integral stainless steel parts.

5. The tool according to claim 1, wherein the control member comprises one of a flexible cable or a rod extending along a channel in the proximal portion.

6. The tool according to claim 1, wherein the proximal portion is malleable such that the fixed arc can be changed by manual force.

7. The tool according to claim 1, wherein the means for applying tension comprises a base at a proximal end of the proximal section and a lever pivotally mounted on the base, the control member being attached to the lever for application of tension to the control member, and the passage providing lateral clearance for displacement of the control member relative to the proximal portion.

8. The tool according to claim 1, wherein the means for applying tension comprises a base at a proximal end of the proximal section and a lever pivotally mounted on the base, the control member being attached to the lever for application of tension to the control member, wherein the proximal portion is bent in a curve in the plane.

9. A tool for assisting in manual placement of an endotracheal tube in a patient such that such an endotracheal tube passes through a mouth, pharynx and larynx of the patient, the tool comprising:

an elongated proximal portion at least partly defining a fixed arc and a longitudinal passage in a plane of the proximal portion, leading from a fixed proximal end toward an articulating distal end of the tool, the proximal portion being substantially rigid;

at least one articulating distal link attached to the distal end of the fixed proximal portion of the tool by a pivot pin defining a pivot axis permitting the articulating link to pivot relative to the proximal portion in said plane;

an elongated control member extending along the proximal portion, the control member passing along an inner side of the pivot axis and being attached to the articulating link; and, means for applying tension to the control member such that the articulating link portion is diverted toward said inner side of the pivot axis, whereby an endotracheal tube can be placed on the tool and guided through the larynx.

10. In combination, an endotracheal tube and a tool for assisting in manual placement of the endotracheal tube in a patient such that the tube passes through a mouth, pharynx and larynx of the patient, the tool comprising:

an elongated proximal portion at least partly defining a fixed arc and passage, the proximal portion being rigidly curved in a fixed arc in a plane of the proximal portion, leading toward an articulating distal end of the tool, the proximal portion being substantially rigid;

an articulating distal link attached to the distal end of the proximal portion of the tool by a pivot pin defining a pivot axis perpendicular to the plane of the proximal portion, thereby permitting the articulating link to pivot relative to the fixed proximal portion in said plane, the endotracheal tube, the fixed proximal portion and the articulating link being dimensioned such that the endotracheal tube can slide onto the tool;

an elongated control member extending through the proximal portion, the control member passing on an inner side of the pivot axis relative to the fixed arc and being attached to the articulating link; and, means for applying tension to the control member such that the articulating link portion is diverted relative to the fixed arc of the substantially rigid proximate portion toward said inner side of the pivot axis in the medial plane, whereby an endotracheal tube can be placed on the tool and guided through the larynx.

11. The combination according to claim 10, wherein the substantially rigid proximal portion and the articulating link portion has an outside diameter equal to 50 to 90% of an internal diameter of the endotracheal tube.

12. The combination according to claim 10, wherein the proximal portion has an outside diameter approximating an internal diameter of the endotracheal tube, with sufficient clearance to permit free sliding of the tool in the endotracheal tube, whereby the endotracheal tube is diverted substantially to a same extent as the articulating link portion.

13. The combination according to claim 10, further comprising a stop disposed on the proximal portion, the stop being placed to position the link at a distal end of the endotracheal tube.

14. The combination according to claim 13, further comprising means for adjusting a position of the stop and fixing the stop in said position.

15. The combination according to claim 10, wherein the articulating link portion is operable to divert the endotracheal tube from a neutral position aligned to the substantially fixed proximal portion to a diverted position wherein a distal end of the endotracheal tube is divertable at least 90° from the neutral position.

16. The combination according to claim 15, wherein the articulating link portion is operable to divert the endotracheal tube in an area of an endmost articulating distal link to greater than 100° anteriorly of said neutral position.

17. The combination according to claim 10, wherein the substantially rigid proximal portion defines a channel receiving the control member for longitudinal displacement and the means for applying tension comprises a lever handle attached to the control member and to a pivot connection with the proximal portion, such that the control member is raised in the channel by pivoting the lever handle.

18. The combination according to claim 10, further comprising a movable stop on the proximal portion for setting a position of the endotracheal tube along the tool.

* * * * *